US008637655B2

(12) United States Patent
Mulero et al.

(10) Patent No.: US 8,637,655 B2
(45) Date of Patent: Jan. 28, 2014

(54) AMELOGENIN SNP ON CHROMOSOME X

(75) Inventors: Julio Mulero, Sunnyvale, CA (US); Robert Green, Cupertino, CA (US); Robert Lagace, Oakland, CA (US); Lori Hennessy, San Mateo, CA (US)

(73) Assignee: Life Technologies Corporation, Carlsbad, CA (US)

( * ) Notice: Subject to any disclaimer, the term of this patent is extended or adjusted under 35 U.S.C. 154(b) by 330 days.

(21) Appl. No.: 12/856,530

(22) Filed: Aug. 13, 2010

(65) Prior Publication Data
US 2011/0237443 A1 Sep. 29, 2011

Related U.S. Application Data

(60) Provisional application No. 61/233,799, filed on Aug. 13, 2009.

(51) Int. Cl.
*C07H 21/04* (2006.01)
*C12P 19/34* (2006.01)

(52) U.S. Cl.
USPC ............................ 536/24.33; 435/91.2

(58) Field of Classification Search
USPC ............................ 536/24.33; 435/91.2
See application file for complete search history.

(56) References Cited

U.S. PATENT DOCUMENTS

| | | | |
|---|---|---|---|
| 5,210,015 A | 5/1993 | Gelfand et al. | |
| 5,599,666 A | 2/1997 | Schumm et al. | |
| 5,674,686 A | 10/1997 | Schumm et al. | |
| 5,783,406 A | 7/1998 | Schumm et al. | |
| 6,531,282 B1 * | 3/2003 | Dau et al. | 435/6.11 |
| 6,780,588 B2 | 8/2004 | Coticone et al. | |
| 6,812,339 B1 | 11/2004 | Venter et al. | |
| 7,008,771 B1 | 3/2006 | Schumm et al. | |
| 2008/0299562 A1 | 12/2008 | Oeth et al. | |
| 2009/0129862 A1 | 5/2009 | Thiel et al. | |

FOREIGN PATENT DOCUMENTS

| | | |
|---|---|---|
| EP | 0487218 | 5/1992 |
| EP | 0512334 | 11/1992 |
| EP | 2113574 | 10/2010 |
| WO | WO2009/132860 | 11/2009 |

OTHER PUBLICATIONS

Birren et al., "Genome Analysis Laboratory Manual Series", B. Birren, ed., *Cold Spring Harbor Laboratory Press*, vols. 1-4, 1997-1999.
International Search Report and Written Opinion, PCT/US 10/45544, completed Feb. 10, 2011.
Sullivan et al., A rapid and quantitative DNA sex test: fluorescence-based PCR analysis of X-Y homologous gene amelogenin. Biotechniques, 1993 vol. 15, No. 4, pp. 636-638, 640-641.
Ouryoubi et al., Analysis of mutations in the amelogenin and enamelin genes in severe carries in Japanese pediatric patients. Pediatric Dental Journal, 2008, vol. 18, No. 2, pp. 79-85.
Applied Biosystems, *AmpFISTR Identifier PCR Amplification Kit User's Manual Applied Biosystems*, 2001, i-x and 1-1 to 1-10.
Blastn results for SEQ ID No. 9 vs. human build 37 genome database; Jul. 21, 2011; 6 pages.
10808855.0, "European Search Report", Oct. 12, 2012, 6 pages.
Cadenas, A.M., "Male Amelogenin Dropouts: Phylogenetic Context, Origins and Implications", *ScienceDirect, Forensic Science International*, vol. 166., 2007, pp. 155-163.
PCT/US2010/045544, "International Preliminary Report on Patentability and Written Opinion of the International Searching Authority", Feb. 14, 2012, 7 pages.

\* cited by examiner

*Primary Examiner* — Kenneth Horlick

(57) ABSTRACT

Disclosed are methods for gender determination in the intron 1 region of the amelogenin locus and a newly discovered single nucleotide polymorphism (SNP) within the X chromosome of the amelogenin locus which can cause allelic dropout. Also disclosed are kits useful in gender determination.

5 Claims, 3 Drawing Sheets

FIGURE 1

```
AMELX-SNP 1                                                  5'ACCCGAGACATTTCTTATC->
AMELX 9096651    TTTGACCATTGTTGCGTTAACAATGCCCTGGGCTCTGTAAAGAATAGTGTGTTGATTCT    60        SEQ ID NO:5
                 TTTGACCATTGTTGCGTTAACAATGCCCTGGGCTCTGTAAAGAATAGTGTGTTGATTCT              SEQ ID NO:9

AMELX-SNP 61                                                 5'ACCCGAGACATTTCTTATC
AMELX 9096711    TTATCCCAGAT------GTTTCTCAAGTGGTCCTGATTTACAGTTCCTACCACCAGTTT   114        SEQ ID NO:8
                                                                                   AAA    SEQ ID NO:5
                 TTATCCCAGAT------GTTTCTCAAGTGGTCCTGATTTACAGTTCCTACCACCAGTTT              SEQ ID NO:7
                                                                           <- 3'GAA        SEQ ID NO:9
                                                                                   ^
AMELX-SNP 115                                   GGGTCAAATTCAAGACTA 5'
AMELX 9096771    CCCAGTTTAAGCTCTGATGGTTGGCCTCAAGCCTGTGTCG-TCCCAGCAGCCTCCCGCCT  173        SEQ ID NO:8
                 CCCAGTTTAAGCTCTGATGGTTGGCCTCAAGCCTGTGTCG-TCCCAGCAGCCTCCCGCCT             SEQ ID NO:6

AMELX-SNP 174                                   GGGTCAAATTCAAGACTA 5'
AMELX 9096831    GGCCACTCTGACTCAGTCTGTCCTCCTAAATATGGC    209       SEQ ID NO:9           SEQ ID NO:7
                 GGCCACTCTGACTCAGTCTGTCCTCCTAAATATGGC    9096861   SEQ ID NO:8           SEQ ID NO:9

SEQ ID NO:8
                                                                                          SEQ ID NO:6
```

FIGURE 2:

```
Chr X_P  1- TGGGCTCTGTAAAGAATAGTGt gtt gattctttatccagat-- --- gt -44   SEQ ID NO: 2
Chr Y.   1- TGGGCTCTGTAAAGAATAGTGggtggattcttcatccaataaagtggt -50      SEQ ID NO: 3
Chr X_V  1- TGGGCTCTGTAAAGAATAGTGt gtt gattctttatccagat-- --- gt -44   SEQ ID NO: 1
Chr X_U  1- TGGGCTCTGTAAAGAATAGTGt gtt gattctttatccagat-- --- gt -44   SEQ ID NO:11
            5'  ————Primer (F)————>

Chr X_P  45- ttctcaagtggtcctgatttacagttcctaccaccagCTTCCCAGTTTAAGCTCTGATg -105  SEQ ID NO: 2
Chr Y.   51- ttctcaagtggtcccaatttacagttcctaccatcagCTTCCCAGTTTAAGCTCTGATg -111  SEQ ID NO: 3
Chr X_V  45- ttctcaagtggtcctgatttacagttcctaccaccagTTTCCCAGTTTAAGCTCTGATg -105  SEQ ID NO: 1
Chr X_U  45- ttctcaagtggtcctgatttacagttcctaccaccagNTTCCCAGTTTAAGCTCTGATg -105  SEQ ID NO:11
                                      3'  ————<Primer (R)————  5'
```

Primer sequences for the Amelogenin chromosome alleles are in uppercase $X_P$ = Predominant, $X_V$ = Variant, $X_U$ = Universal base (N) in the Primer

FIGURE 3:

```
AMELX-SNP    1  TTTGACCATTGTTTGCGTTAACAATGCCCTGGGCTCTGTAAAGAATAGTGTGTTGATTCT  60     SEQ ID NO:9
                ||||||||||||||||||||||||||||||||||||||||||||||||||||||||||||
AMELX  9096651  TTTGACCATTGTTTGCGTTAACAATGCCCTGGGCTCTGTAAAGAATAGTGTGTTGATTCT  9096710 SEQ ID NO:8
                |||| || ||||||| ||| ||  ||||||||||||||||||||||||| || |||||||
AMELY  4088505  TTTGATCACTGTTTGCATTAGCAGTAGCCCCCTGGGCTCTGTAAAGAATAGTGGGATTCT  4088446 SEQ ID NO:10

AMELX-SNP   61  TTATCCCAGAT------GTTTCTCAAGTGGTCCTGATTTTACAGTTCCTACCACCAGTTT  114    SEQ ID NO:9
                |||||||||||      |||||||||||||||||||||||||||||||||||||||
AMELX  9096711  TTATCCCAGAT------GTTTCTCAAGTGGTCCTGATTTTACAGTTCCTACCACCAGCTT  9096770 SEQ ID NO:8
                ||||||||||                                ||||||||||||||||
AMELY  4088445  TCATCCCAAATAAAGTGGTTTCTCAAGTGGTCCCAATTTTACAGTTTCTACCATCAGCTT  4088386 SEQ ID NO:10
                                                                        ^
AMELX-SNP  115  CCCAGTTTAAGCTCTGATGGTTGGCCTCAAGCCTGTGTCG-TCCCAGCAGCCTCCCGCCT  173    SEQ ID NO:9
                ||||||||||||||||||||||||||||||||||||||| ||||||||||||||||||||
AMELX  9096771  CCCAGTTTAAGCTCTGATGGTTGGCCTCAAGCCTGTGTCG-TCCCAGCAGCCTCCCGCCT  9096830 SEQ ID NO:8
                |||||||||||||||||||||||||||||||||||| ||| |||| ||||||||||||
AMELY  4088385  CCCAGTTTAAGCTCTGATGGTTGGCCTCAAGCCTGTGTTGCTCC-AGCACCCTCCTGCCT  4088327 SEQ ID NO:10

AMELX-SNP  174  GGCCACTCTGACTCAGTCTGTCCTCCTAAATATGGC      209   SEQ ID NO:9
                ||||||||||||||||||||||||||||||||||||
AMELX  9096831  GGCCACTCTGACTCAGTCTGTCCTCCTAAATATGGC      9096861 SEQ ID NO:8
                  ||| |||  || |||||||| ||||||||||||
AMELY  4088326  GACCATTCGGATTGACTCTTTCCTCCTAAATATGGC      4088291 SEQ ID NO:10
```

(primer binding sites are underlined and SNP is indicated by the ^ at position 112 of AMELX-SNP)

SEQUENCE LISTING

```
<160> NUMBER OF SEQ ID NOS: 14

<210> SEQ ID NO 1
<211> LENGTH: 104
<212> TYPE: DNA
<213> ORGANISM: Homo sapiens

<400> SEQUENCE: 1
tgggctctgt aaagaatagt gtgttgattc tttatcccag atgtttctca agtggtcctg      60
attttacagt tcctaccacc agtttcccag tttaagctct gatg                      104

<210> SEQ ID NO 2
<211> LENGTH: 104
<212> TYPE: DNA
<213> ORGANISM: Homo sapiens

<400> SEQUENCE: 2
tgggctctgt aaagaatagt gtgttgattc tttatcccag atgtttctca agtggtcctg      60
attttacagt tcctaccacc agcttcccag tttaagctct gatg                      104
```

```
<210> SEQ ID NO 3
<211> LENGTH: 110
<212> TYPE: DNA
<213> ORGANISM: Homo sapiens

<400> SEQUENCE: 3
tgggctctgt aaagaatagt gggtggattc ttcatcccaa ataaagtggt ttctcaagtg    60
gtcccaattt tacagttcct accatcagct tcccagttta agctctgatg              110

<210> SEQ ID NO 4
<211> LENGTH: 21
<212> TYPE: DNA
<213> ORGANISM: Homo sapiens
<220> FEATURE:
<221> NAME/KEY: modified_base
<222> LOCATION: (21)..(21)
<223> OTHER INFORMATION: Universal base

<400> SEQUENCE: 4
atcagagctt aaactgggaa n                                              21

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
acccgagaca tttcttatc                                                 19

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
atcagagctt aaactgggaa g                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
atcagagctt aaactgggaa a                                              21

<210> SEQ ID NO 8
<211> LENGTH: 209
<212> TYPE: DNA
<213> ORGANISM: Homo sapiens

<400> SEQUENCE: 8
tttgaccatt gtttgcgtta acaatgccct gggctctgta aagaatagtg tgttgattct    60
ttatcccaga tgtttctcaa gtggtcctga ttttacagtt cctaccacca gcttcccagt   120
ttaagctctg atggttggcc tcaagcctgt gtcgtcccag cagcctcccg cctggccact   180
ctgactcagt ctgtcctcct aaatatggc                                     209
```

```
<210> SEQ ID NO 9
<211> LENGTH: 209
<212> TYPE: DNA
<213> ORGANISM: Homo sapiens

<400> SEQUENCE: 9
tttgaccatt gtttgcgtta acaatgccct gggctctgta aagaatagtg tgttgattct      60
ttatcccaga tgtttctcaa gtggtcctga ttttacagtt cctaccacca gtttcccagt     120
ttaagctctg atggttggcc tcaagcctgt gtcgtcccag cagcctcccg cctggccact     180
ctgactcagt ctgtcctcct aaatatggc                                       209

<210> SEQ ID NO 10
<211> LENGTH: 215
<212> TYPE: DNA
<213> ORGANISM: Homo sapiens

<400> SEQUENCE: 10
tttgatcact gtttgcatta gcagtccct gggctctgta aagaatagtg ggtggattct       60
tcatcccaaa taaagtggtt tctcaagtgg tcccaatttt acagttccta ccatcagctt    120
cccagtttaa gctctgatgg ttggcctcaa gcctgtgttg ctccagcacc ctcctgcctg    180
accattcgga ttgactcttt cctcctaaat atggc                                215

<210> SEQ ID NO 11
<211> LENGTH: 104
<212> TYPE: DNA
<213> ORGANISM: Homo sapiens
<220> FEATURE:
<221> NAME/KEY: modified_base
<222> LOCATION: (83)..(83)
<223> OTHER INFORMATION: Universal base

<400> SEQUENCE: 11
tgggctctgt aaagaatagt gtgttgattc tttatcccag atgtttctca agtggtcctg      60
attttacagt tcctaccacc agnttcccag tttaagctct gatg                      104

<210> SEQ ID NO 12
<211> LENGTH: 21
<212> TYPE: DNA
<213> ORGANISM: Homo sapiens

<400> SEQUENCE: 12
atcatcatca tcaacatcat c                                                21

<210> SEQ ID NO 13
<211> LENGTH: 20
<212> TYPE: DNA
<213> ORGANISM: Homo sapiens

<400> SEQUENCE: 13
gatagataga tacatagata                                                  20

<210> SEQ ID NO 14
<211> LENGTH: 15
<212> TYPE: DNA
<213> ORGANISM: Homo sapiens

<400> SEQUENCE: 14
attgcattgc attgc                                                       15
```

AMELOGENIN SNP ON CHROMOSOME X

FIELD

In general, the disclosed invention relates to the identification of a single nucleotide polymorphism (SNP) in the amelogenin locus on human chromosome X.

BACKGROUND

The fields of forensics, paternity testing, tissue typing, and personalized medicine routinely use DNA-based techniques for identity determinations, genotyping, phenotypic prediction, and in the prediction and/or prevention of disease. The use of DNA to establish or disprove a defendant's connection to a crime scene sample has been pivotal in analysis of the evidence in criminal proceedings. Frequently, it is not only the autosomal DNA, but DNA associated with the sex chromosomes, X and/or Y, in establishing a defendant's guilt or innocence.

Amelogenin is a protein involved in the production of tooth enamel. In many mammals there exists a copy of the gene on the X chromosome (AMELX) and another copy on the Y chromosome (AMELY). Differences in the Amelogenin DNA sequence between the sex chromosomes have allowed the development of gender determination tests. The differences are easily discerned in a polymerase chain reaction (PCR) in which a single primer pair simultaneously amplifies the DNA from each chromosome revealing different sized fragments. A PCR primer pair can be designed to flank a 6 basepair (bp) deletion found in the amelogenin gene on the X chromosome. The resulting PCR fragment on the X chromosome is 6 bp shorter than the corresponding Y chromosome's fragment.

Accurate DNA analysis has both solved missing persons and exonerated the innocent. The adoption of DNA test results has established DNA-base methodologies as a standard investigative, diagnostic or prognostic tool depending on the application. Alterations in the DNA sequence can occur via mutations, polymorphisms or re-arrangements, for example. The identification of such alterations can be useful in the continued effort to maintain the sensitivity, specificity, quality and reliability of DNA-based technologies. Thus, there exists a need in the art, to improve DNA-based technologies based on the discovery of a new variation in a DNA sequence.

SUMMARY OF SOME EMBODIMENTS OF THE INVENTION

In some embodiments, disclosed is a method for gender determination comprising: binding a first primer to a first amelogenin primer binding site in a target nucleic acid sequence; binding a second primer to a second amelogenin primer binding site in said target nucleic acid sequence; wherein said second primer binds to a single nucleotide polymorphism (SNP) in said target sequence; amplifying said target nucleic acid, wherein the amplifying yields at least a first amplified sequence; and detecting the at least said first amplified sequence. In the detecting step, detection of only the first amplified sequence indicates female gender and detection of the first and a second amplified sequences indicates male gender, wherein the first amplified sequence and the second amplified sequence differ in length and the first amplified sequence is six basepairs shorter than said second amplified sequence.

In some embodiments a SNP corresponding to position 83 of SEQ ID NO:1 (variant) causes allelic dropout of the X chromosome amelogenin allele when amplified but not SEQ ID NO:2 (predominant) nor SEQ ID NO:3, lacking the SNP, corresponding to the Y chromosome of amelogenin and the second primer is capable of annealing to SEQ ID NO: 1, SEQ ID NO:2 and SEQ ID NO:3. However, inclusion of a universal base that hybridizes to position 83 of both SEQ ID NO:1 and SEQ ID NO:2 can avoid allelic dropout, and depending on the primer binding site, the universal base can be located at the 3' terminus nucleobase of the first primer, at the base before the 3' terminus nucleobase of the first primer, two bases before the 3' terminus nucleobase of the first primer, or three, four, five, six, seven, eight, nine nucleobases before the 3' terminus nucleobase as well as at any position within the first primer that would basepair with the position 83 of SEQ ID NO:1 and SEQ ID NO:2, as illustrated in FIG. 2.

In some embodiments, the universal base is selected from the group consisting of Inosine, Xanthosine, 3-nitropyrrole, 4-nitroindole, 5-nitroindole, 6-nitroindole, nitroimidazole, 4-nitropyrazole, 5-aminoindole, 4-nitrobenzimidazole, 4-aminobenzimidazole, phenyl C-ribonucleoside, benzimidazole, 5-fluoroindole, indole; acyclic sugar analogs, derivatives of hypoxanthine, imidazole 4,5-dicarboxamide, 3-nitroimidazole, 5-nitroindazole; aromatic analogs, benzene, naphthalene, phenanthrene, pyrene, pyrrole, difluorotoluene; isocarbostyril nucleoside derivatives, MICS, ICS; and hydrogen-bonding analogs, N8-pyrrolopyridine.

In some embodiments, the second primer comprises SEQ ID NO:6 or SEQ ID NO:7 or SEQ ID NO:4 and the complements thereof, and either of the first primer (SEQ ID NO:5) or the second primer can further comprise a label which can be fluorescent. Said fluorescent label can have a label including but not limited to a fluorescent label selected from 5-carboxyfluorescein (FAM™ dye), and 2'7'-dimethoxy-4'5'-dichloro-6-carboxyfluorescein (JOE™ dye), fluorescein (FL); N,N,N', N'-tetramethyl-6-carboxyrhodamine (TAMRA™ dye); 6-carboxy-X-rhodamine (ROX™ dye); CY3™ dye; CY5™ dye; tetrachloro-fluorescein (TET™ dye); and hexachloro-fluorescein (HEX™ dye); NED™ dye; 6-FAM™ dye; VIC® dye; PET® dye; LIZ™ dye, SID™ dye, TED™ dye, and TAZ™ dye.

In some embodiments, disclosed is a method for gender determination having the method of: annealing at least a first primer to at least a first primer binding site in a target nucleic acid sequence; annealing at least a second primer to at least a second primer binding site; optionally, annealing a third primer specific to a single nucleotide polymorphism (SNP) on chromosome X; amplifying said target nucleic acid, wherein the amplifying yields at least a first amplified sequence; and detecting the least first amplified sequence. When the detecting step detects only the first amplified sequence it indicates female gender and when detection includes the first and a second amplified sequence, this indicates male gender. The single nucleotide polymorphism (SNP) corresponds to position 83 of SEQ ID NO:1 and SEQ ID NO:2 and SEQ ID NO:1 corresponds to the variant SNP "T" containing sequence while SEQ ID NO:2 corresponds to the wildtype/predominant "C" containing sequence on chromosome X. The detection of SEQ ID NO:3 corresponds to the corresponding region on the Y chromosome of the intron 1 region of the amelogenin gene and is six basepairs longer than the corresponding amplicon region for the X chromosome (FIG. 2). The first primer is designed to anneal to SEQ ID NO: 1 and SEQ ID NO:2 (SEQ ID NOS: 4, 6 and 7) while the second primer is capable of annealing to SEQ ID NO: 1, SEQ ID NO:2 and SEQ ID NO:3 (SEQ ID NO:5 as shown in FIG.

1 and Table 1). The primer sequences are further illustrated in Table 1. At least one of the primers in a primer pair can be labeled with a label, including a fluorescent label.

In some embodiments, a method for co-amplifying a plurality of loci, including but not limited to polymorphic loci such as SNP and STR loci and the Amelogenin locus in a multiplex amplification reaction is disclosed, wherein the product of the reaction is a mixture of a plurality of amplified alleles from each of the co-amplified loci; and evaluating the plurality of amplified alleles in the mixture to determine the alleles present at each of the loci analyzed. The method can further have the step of separating the amplified alleles prior to the evaluating step included, but not limited to, separation by capillary gel electrophoresis.

The co-amplifying step of the multiplex amplification reaction can have one pair of oligonucleotide primers for each of the loci and at least one primer of each pair of oligonucleotide primers is a labeled primer. The label can be a fluorescent label and the reaction can have at least five fluorescently labeled oligonucleotide primers for at least five different loci, wherein the at least five labeled primers have at least five different fluorescent labels respectively attached thereto. The label can be covalently attached to the primer. Also envisioned is a co-amplifying step comprises using at least six fluorescently labeled oligonucleotide primers, wherein the at least six labeled primers have at least six different fluorescent labels respectively covalently attached thereto. The at least six different fluorescent labels can have a first fluorescent label which emits its maximum fluorescence between 480-520 nm, a second fluorescent label which emits its maximum fluorescence between 525-550 nm, a third fluorescent label which emits its maximum fluorescence between 555-575 nm, a fourth fluorescent label which emits its maximum fluorescence between 580-590 nm, a fifth fluorescent label which emits its maximum fluorescence between 625-650 nm, and a sixth fluorescent label which emits its maximum fluorescence between 595-620 nm.

The plurality of polymorphic loci such as SNP and STR loci and the Amelogenin locus can be co-amplified using a polymerase chain reaction and the loci are from at least one biological sample such as human tissue or human fluid selected from one or more of the group consisting of blood, feces, semen, vaginal cells, hair, saliva, urine, tooth, bone, buccal sample, amniotic fluid containing placental cells, and amniotic fluid containing fetal cells.

In other embodiments, included are kits for gender determination having: a first primer with a 3' terminus nucleotide capable of hybridizing to a first primer binding site including position 83 of SEQ ID NO:1 or its complement, a second primer with a 3' terminus nucleotide capable of hybridizing to a second primer binding site which includes position 83 of SEQ ID NO:2 or its complement and to the corresponding primer binding site found in SEQ ID NO:3 for the Y chromosome, and a third primer which hybridizes upstream of position 83 of SEQ ID NO:1 and SEQ ID NO:2 and the corresponding region in SEQ ID NO:3; wherein said primers are used in a PCR reaction and wherein amplification products from both SEQ ID NO:1 and SEQ ID NO:3 or SEQ ID NO:2 and SEQ ID NO:3 determines the gender as male and an amplification product from only SEQ ID NO:1 or SEQ ID NO:2 determines the gender as female. The kit can further comprise a polymerase.

The kit can also have a first primer set which hybridizes to chromosome X and a second primer set which hybridizes to chromosome Y; wherein said primers are used in a PCR reaction and wherein amplification products from both said first and said second primer sets determines the gender as male and an amplification product from only said first primer set determines the gender as female.

The primer sets can have a third primer having the sequence ACCCGAGACATTTCTTATC (SEQ ID NO:5); a second primer having the sequence ATCAGAGCT-TAAACTGGGAAG (SEQ ID NO:6); and a first primer having the sequence of ATCAGAGCTTAAACTGGGAAA (SEQ ID NO:7) or the complementary sequence of any of these primers. The sequence ATCAGAGCTTAAACTGG-GAAN (SEQ ID NO:4) can be paired with SEQ ID NO:5 and SEQ ID NO:5: can be paired with SEQ ID NO:6 and SEQ ID NO:7. The "N" in SEQ ID NO:4 denotes a universal base which can hybridize to position 83 of either SEQ ID NO:1 or SEQ ID NO:2. The "N" universal base can be at any position within a primer sequence that hybridizes to a target nucleic acid sequence which includes position 83 of either SEQ ID NO:1 or SEQ ID NO:2. The primers are used in PCR.

The amplicon generated when primer sequences SEQ ID NOS: 5 and 6 are used together to amplify SEQ ID NO:3 is longer by six basepairs than when primers SEQ ID NOS: 5 and 6 or primers SEQ ID NOS:5 and 7 are used together to amplify SEQ ID NO:2 or SEQ ID NO:1, respectively. In this instance, the amplicon of SEQ ID NO:3 is about 109 basepairs in length and the amplicon of SEQ ID NOS:2 and 1 is about 103 basepairs in length and the amplicon of SEQ ID NO: 3 corresponds to a region of chromosome Y and the amplicon of SEQ ID NOS: 2 and 1 amplify a region of chromosome X.

DESCRIPTION OF EXEMPLARY EMBODIMENTS

For the purposes of interpreting of this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). It is noted that, as used in this specification and the appended claims, the singular forms "a," "an," and "the," include plural referents unless expressly and unequivocally limited to one referent. The use of "or" means "and/or" unless stated otherwise. For illustration purposes, but not as a limitation, "X and/or Y" can mean "X" or "Y" or "X and Y". The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of". The term "and/or" means one or all of the listed elements or a combination of any two or more of the listed element.

The section headings used herein are for organizational purposes only and are not to be construed as limiting the described subject matter in any way. All literature cited in this specification, including but not limited to, patents, patent applications, articles, books, and treatises are expressly incorporated by reference in their entirety for any purpose. In the event that any of the incorporated literature contradicts any term defined herein, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

BRIEF DESCRIPTION OF THE DRAWINGS

The skilled artisan will understand that the drawings described below are for illustration purposes only. The drawings are not intended to limit the scope of the present teachings in any way.

FIG. 1 depicts the amplification of a region of intron 1 of the human Amelogenin gene from the X chromosome and indicates the mispriming at the 3' terminus when a gene mutation is present, resulting in allelic dropout. The gene mutation is indicated in bold and the underlining indicates primer binding regions.

FIG. 2 illustrates amplicons for intron 1 of the Amelogenin locus

FIG. 3 is a partial alignment of intron 1 of the Amelogenin gene from the X and Y chromosomes and the newly discovered SNP within the X chromosome.

The practice of the present invention may employ conventional techniques and descriptions of organic chemistry, polymer technology, molecular biology (including recombinant techniques), cell biology, biochemistry, and immunology, which are within the skill of the art. Such conventional techniques include oligonucleotide synthesis, hybridization, extension reaction, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), PCR Primer: A Laboratory Manual, and Molecular Cloning: A Laboratory Manual (all from Cold Spring Harbor Laboratory Press, 1989), Gait, "Oligonucleotide Synthesis: A Practical Approach" 1984, IRL Press, London, Nelson and Cox (2000), Lehninger, Principles of Biochemistry $3^{rd}$ Ed., W. H. Freeman Pub., New York, N.Y. and Berg et al. (2002) Biochemistry, $5^{th}$ Ed., W. H. Freeman Pub., New York, N.Y. all of which are herein incorporated in their entirety by reference for all purposes.

The term "allelic ladder" as used herein refers to a standard size marker comprising a plurality of amplified alleles from a genetic marker.

The term "allele" as used herein refers to a genetic variation associated with a gene or a segment of DNA, i.e., one of two or more alternate forms of a DNA sequence occupying the same locus.

The term "locus" as used herein refers to a specific position on a chromosome or a nucleic acid molecule. Alleles of a locus are located at identical sites on homologous chromosomes. "Loci" is the plural of locus.

The terms "amplicon" and "amplification product" as used herein refer to a broad range of techniques for increasing polynucleotide sequences, either linearly or exponentially and can be the product of an amplification reaction. An amplicon can be double-stranded or single-stranded, and can include the separated component strands obtained by denaturing a double-stranded amplification product. In certain embodiments, the amplicon of one amplification cycle can serve as a template in a subsequent amplification cycle. Exemplary amplification techniques include, but are not limited to, PCR or any other method employing a primer extension step. Other nonlimiting examples of amplification include, but are not limited to, ligase detection reaction (LDR) and ligase chain reaction (LCR). Amplification methods can comprise thermal-cycling or can be performed isothermally. In various embodiments, the term "amplification product" includes products from any number of cycles of amplification reactions.

Also herein, the recitations of numerical ranges by endpoints include all numbers subsumed within that range (e.g., 1 to 5 includes 1, 1.5, 2, 2.75, 3, 3.80, 4, 5, etc.).

As used herein, "DNA" refers to deoxyribonucleic acid in its various forms as understood in the art, such as genomic DNA, cDNA, isolated nucleic acid molecules, vector DNA, and chromosomal DNA. "Nucleic acid" refers to DNA or RNA in any form. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA molecules. Typically, an "isolated" nucleic acid is free of sequences which naturally flank the nucleic acid (i.e., sequences located at the 5' and 3' ends of the nucleic acid) in the genomic DNA of the organism from which the nucleic acid is derived. Moreover, an "isolated" nucleic acid molecule, such as a cDNA molecule, is generally substantially free of other cellular material or culture medium when produced by recombinant techniques, or free of chemical precursors or other chemicals when chemically synthesized.

The terms "detecting" and "detection" are used in a broad sense herein and encompass any technique by which one can determine the presence or identify a nucleic acid sequence. In some embodiments, detecting comprises quantitating a detectable signal from the nucleic acid, including without limitation, a real-time detection method, such as quantitative PCR ("Q-PCR"). In some embodiments, detecting comprises determining the sequence of a sequencing product or a family of sequencing products generated using an amplification product as the template; in some embodiments, such detecting comprises obtaining the sequence of a family of sequencing products.

As used herein, "forward" and "reverse" are used to indicate relative orientation of primers on a polynucleotide sequence. For illustration purposes but not as a limitation, consider a single-stranded polynucleotide drawn in a horizontal, left to right orientation with its 5'-end on the left. The "reverse" primer is designed to anneal with the downstream primer-binding site at or near the "3'-end" of this illustrative polynucleotide in a 5' to 3' orientation, right to left. The corresponding "forward primer is designed to anneal with the complement of the upstream primer-binding site at or near the "5'-end" of the polynucleotide in a 5' to 3' "forward" orientation, left to right. Thus, the reverse primer comprises a sequence that is complementary to the reverse or downstream primer-binding site of the polynucleotide and the forward primer comprises a sequence that is the same as the forward or upstream primer-binding site. It is to be understood that the terms "3-end" and "5'-end" as used in this paragraph are illustrative only and do not necessarily refer literally to the respective ends of the polynucleotide. Rather, the only limitation is that the reverse primer of this exemplary primer pair anneals with a reverse primer-binding site that is downstream or to the right of the forward primer-binding site that comprises the same sequence as the corresponding forward primer. As will be recognized by those of skill in the art, these terms are not intended to be limiting, but rather to provide illustrative orientation in a given embodiment.

As used herein, the terms "hybridization" and "anneal" are used interchangeably and refer to the pairing of complementary nucleic acid strands. Hybridization and the strength of hybridization (i.e., the strength of the association between nucleic acid strands) is impacted by many factors well known in the art including, but not limited to, the degree of complementarity between the nucleic acids, stringency of the conditions involved, the presence of other components (e.g., the presence or absence of polyethylene glycol), the molarity of the hybridizing strands, the G:C content of the nucleic acid strands, and so on.

The term "selectively hybridize" and variations thereof means that, under appropriate stringency conditions, a given sequence (for example, but not limited to, a primer) anneals with a second sequence comprising a complementary string of nucleotides (for example, but not limited to, a target flanking sequence or a primer-binding site of an amplicon), but does not anneal to undesired sequences, such as non-target nucleic acids or other primers. Typically, as the reaction temperature increases toward the melting temperature of a particular double-stranded sequence, the relative amount of selective hybridization generally increases and mis-priming generally decreases. A statement that one sequence hybridizes or selectively hybridizes with another sequence encompasses embodiments where the entirety of both of the sequences hybridize to one another and embodiments where only a portion of one or both of the sequences hybridizes to the entire other sequence or to a portion of the other sequence.

As used herein, the term "marker" refers to the mutation in a gene which facilitates the study of its inheritance.

As used herein, the term "gene mutation" refers to a change within a single gene giving rise to alternative genes or alleles. Gene mutations are inherited changes.

As used herein, the term "point mutation" refers to a single nucleotide base pair change in DNA. The point mutation is a gene mutation resulting from the substitution, addition, or deletion of one or a few bases (nucleobases). The point mutation can become stabilized within a genome upon replication past the altered site.

As used herein, the term "stringency" refers to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required when it is desired that nucleic acids which are not completely complementary to one another be hybridized or annealed together. The art knows well that numerous equivalent conditions can be employed to comprise low stringency conditions.

As used herein, the term "homology" refers to a degree of complementarity. There can be partial homology or complete homology (i.e., identity). A partially complementary sequence that at least partially inhibits a completely complementary sequence from hybridizing to a target nucleic acid is referred to using the functional term "substantially homologous."

As used herein, the terms "polynucleotide", "oligonucleotide", and "nucleic acid" are used interchangeably and refer to single-stranded and double-stranded polymers of nucleotide monomers, including without limitation 2'-deoxyribonucleotides (DNA) and ribonucleotides (RNA) linked by internucleotide phosphodiester bond linkages, or internucleotide analogs, and associated counter ions, e.g., $H^+$, $NH_4^+$, trialkylammonium, $Mg^{2+}$, $Na^+$, and the like. A polynucleotide may be composed entirely of deoxyribonucleotides, entirely of ribonucleotides, or chimeric mixtures thereof and can include nucleotide analogs. The nucleotide monomer units may comprise any nucleotide or nucleotide analog. Polynucleotides typically range in size from a few monomeric units, e.g. 5-40 when they are sometimes referred to in the art as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytosine, "G" denotes deoxyguanosine, "T" denotes thymidine, and "U" denotes deoxyuridine, unless otherwise noted.

As used herein, the terms "target polynucleotide," "nucleic acid target" and "target nucleic acid" are used interchangeably and refer to a particular nucleic acid sequence of interest. The "target" can be a polynucleotide sequence that is sought to be amplified and can exist in the presence of other nucleic acid molecules or within a larger nucleic acid molecule. The target polynucleotide can be obtained from any source, and can comprise any number of different compositional components. For example, the target can be nucleic acid (e.g. DNA or RNA). The target can be methylated, non-methylated, or both. Further, it will be appreciated that "target polynucleotide" can refer to the target polynucleotide itself, as well as surrogates thereof, for example amplification products, and native sequences. In some embodiments, the target polynucleotide is a short DNA molecule derived from a degraded source, such as can be found in, for example, but not limited to, forensics samples (see for example Butler, 2001, Forensic DNA Typing: Biology and Technology Behind STR Markers). The target polynucleotides of the present teachings can be derived from any of a number of sources. These sources may include, but are not limited to, whole blood, a tissue biopsy, lymph, bone, bone marrow, tooth, amniotic fluid, hair, skin, semen, anal secretions, vaginal secretions, perspiration, saliva, buccal swabs, various environmental samples (for example, agricultural, water, and soil), research samples generally, purified samples generally, and lysed cells. It will be appreciated that target polynucleotides can be isolated from samples using any of a variety of procedures known in the art, for example the PrepSEQ™ Kits (from Applied Biosystems), Boom et al., and U.S. Pat. No. 5,234,809, etc. It will be appreciated that target polynucleotides can be cut or sheared prior to analysis, including the use of such procedures as mechanical force, sonication, restriction endonuclease cleavage, or any method known in the art.

As used herein, the "polymerase chain reaction" or PCR is a an amplification of nucleic acid consisting of an initial denaturation step which separates the strands of a double stranded nucleic acid sample, followed by repetition of (i) an annealing step, which allows amplification primers to anneal specifically to positions flanking a target sequence; (ii) an extension step which extends the primers in a 5' to 3' direction thereby forming an amplicon polynucleotide complementary to the target sequence, and (iii) a denaturation step which causes the separation of the amplicon from the target sequence (Mullis et al., eds, The Polymerase Chain Reaction, BirkHauser, Boston, Mass. (1994)). Each of the above steps may be conducted at a different temperature, preferably using an automated thermocycler (Applied Biosystems LLC, a division of Life Technologies Corporation, Foster City, Calif.). If desired, RNA samples can be converted to DNA/RNA heteroduplexes or to duplex cDNA by methods known to one of skill in the art. The PCR method also includes reverse transcriptase-PCR and other reactions that follow principles of PCR.

The term "primer" refers to a polynucleotide and analogs thereof that are capable of selectively hybridizing to a target nucleic acid or "template", a target region flanking sequence or to a corresponding primer-binding site of an amplification product; and allows the synthesis of a sequence complementary to the corresponding polynucleotide template, flanking sequence or amplification product from the primer's 3' end. Typically a primer can be between about 10 to 100 nucleotides in length and can provide a point of initiation for template-directed synthesis of a polynucleotide complementary to the template, which can take place in the presence of appropriate enzyme(s), cofactors, substrates such as nucleotides and the like.

As used herein, the term "amplification primer" refers to an oligonucleotide, capable of annealing to an RNA or DNA region adjacent a target sequence, and serving as an initiation primer for DNA synthesis under suitable conditions well known in the art. Typically, a PCR reaction employs a pair of amplification primers including an "upstream" or "forward" primer and a "downstream" or "reverse" primer, which delimit a region of the RNA or DNA to be amplified.

As used herein, the term "primer-binding site" refers to a region of a polynucleotide sequence, typically a sequence flanking a target region and/or an amplicon that can serve directly, or by virtue of its complement, as the template upon which a primer can anneal for any suitable primer extension reaction known in the art, for example, but not limited to, PCR. It will be appreciated by those of skill in the art that when two primer-binding sites are present on a single polynucleotide, the orientation of the two primer-binding sites is generally different. For example, one primer of a primer pair is complementary to and can hybridize with the first primer-binding site, while the corresponding primer of the primer pair is designed to hybridize with the complement of the second primer-binding site. Stated another way, in some embodiments the first primer-binding site can be in a sense orientation, and the second primer-binding site can be in an antisense orientation. A primer-binding site of an amplicon may, but need not comprise the same sequence as or at least some of the sequence of the target flanking sequence or its complement.

Those in the art understand that as a target region is amplified by certain amplification means, the complement of the primer-binding site is synthesized in the complementary amplicon or the complementary strand of the amplicon. Thus, it is to be understood that the complement of a primer-binding site is expressly included within the intended meaning of the term primer-binding site, as used herein.

As used herein, the term "single nucleotide polymorphism" or SNP, refers to a variation from the most frequently occurring base at a particular nucleic acid position.

As used herein, the term "short tandem repeat (STR) loci" refers to regions of the human genome which contains short, repetitive sequence elements of 3 to 7 basepairs in length. The repeats at a given STR marker do not need to be perfect repeats. Examples of STRs, include but are not limited to, a triplet repeat; atcatcatcatcaacatcatc, a 4-peat; gatagatagatacatagata, and a 5-peat; attgcattgcattgc and so on.

As used herein, the term "Polymorphic short tandem repeat loci" refers to STR loci in which the number of repetitive sequence elements (and net length of sequence) in a particular region of genomic DNA varies from allele to allele, and from individual to individual.

As used herein, the terms "polymorphism" and "DNA polymorphism" generally refer to the condition in which two or more different nucleotide sequences in a DNA sequence coexist in the same interbreeding population.

As used herein, the term "genome" refers to the complete DNA sequence, containing the entire genetic information, of a gamete, an individual, a population, or a species.

As used herein, the term "genomic DNA" refers to the chromosomal DNA sequence of a gene or segment of a gene, including the DNA sequence of noncoding as well as coding regions. Genomic DNA also refers to DNA isolated directly from cells or chromosomes or the cloned copies of all or part of such DNA.

As used herein, the term "chromosome" broadly refers to autosomes and sex chromosomes. For example, *Homo sapiens* contains 22 autosomes and 2 sex chromosomes, generally, either two X chromosomes or one X and one Y chromosome. The sex chromosomes determine an individual's gender. The male gender is normally imparted on an individual with a single X chromosome and a single Y chromosome whereas female gender is normally recognized when an individual has two X chromosomes. As described herein, the identification of a nucleic acid locus specific to either the X or the Y chromosome can be used to determine gender.

As used herein, the terms "gender" and "sex" refer to the two major forms of individuals of a species and can be distinguished respectively as + and − or male and female based on structures, chromosome identification and reproductive organs. The analysis of a biological sample from an individual of a species using DNA-methodologies can be used in the determination of gender based on the composition of a chromosome.

As used herein, the term "identity" refers to the identification of the gender and/or of the individual where a sample or biological sample originated.

As used herein, the term "universal base" in general refers to a base that can bind to two or more different nucleotide bases present in genomic DNA, without any substantial discrimination, for example a base that can combine with two bases is universal. Examples of universal bases include, but are not limited to, Inosine, Xanthosine, 3-nitropyrrole, 4-nitroindole, 5-nitroindole, 6-nitroindole, and so on.

The term "universal base" refers to a base analog that forms "basepairs" with each of the natural DNA or RNA bases with sufficient affinity to provide for the desired level of hybridization affinity in the oligonucleotide primer of interest.

The term "promiscuous (indiscriminative) base" refers to a natural base or a natural base analog that in addition to the perfect complement match base, forms two hydrogen bonds with two or more natural mismatched bases in DNA or RNA with little discrimination between them.

What is disclosed herein are various methods and compositions for determining the gender of a human. The human's gender can be determined by analysis of the nucleic acid found in a sample, including but not limited to a biological sample. A biological sample can be from a known or unknown source and the gender so identified can be used to support identification of rapists, human identification, maternity, paternity, familial relationship, phenotype, tissue compatibility, genetic predisposition to disease, transmission of a genotype, and so on.

Suitable biological samples according to the present invention include, but are not limited to, for example, hair, feces, blood, tissue, urine, saliva, cheek cells, skin, for example skin cells contained in fingerprints, bone, tooth, and semen. It is contemplated that samples may be collected invasively or noninvasively. The sample can be on, in, within, from or found in conjunction with a fiber, fabric, cigarette, chewing gum, adhesive material, soil or inanimate objects. "Sample" as used herein, is used in its broadest sense and refers to a sample suspected of containing a nucleic acid and can comprise a cell, chromosomes isolated from a cell (e.g., a spread of metaphase chromosomes), genomic DNA, RNA, cDNA and the like. The contiguous string of nucleotides, i.e., polynucleotides, comprises an allele which is found in a gene which resides in a position, called a locus, which is within a chromosome.

In some embodiments, the present teachings provide a newly identified single nucleotide polymorphism (SNP) within intron 1 of the Amelogenin gene within the X chromosome. The SNP was discovered while evaluating nucleic acid samples from 1025 separate human individuals. Two out of the 1025 samples were identified as having a previously unknown SNP at the primer binding site on the X chromosome. Further analysis by cloning and sequencing the Amelogenin locus of the two individuals and comparison with the X chromosome reference sequence from GenBank lead to the discovery of the presence of a variant nucleobase corresponding to position 11,225,000 on the X chromosome (GenBank Acc. No. NT_011757.15 (Build 36.3)). The naturally occurring, predominant or wildtype nucleobase is cytidine (C) while the variant nucleobase (i.e., the SNP) is an thymidine (T) as shown in SEQ ID NO:1 and FIG. 2. Failure to amplify the X chromosome Amelogenin locus in the two samples was caused by the present of the variant "T" nucleobase, leading to allelic dropout (FIG. 1).

A mutation in a possible primer binding site within the Amelogenin locus on the X chromosome was identified in the two samples from two different individuals that had X allele allelic dropout. "Allelic dropout" as used herein refers to the failure to amplify a target nucleic acid. Allelic dropout can result from failure of a primer to bind at the primer's 3' terminus to the primer binding site of a target nucleic acid. As a result there is no amplification of the target nucleic acid.

As illustrated in FIG. 2, the target nucleic acid sequence within intron 1 of the Amelogenin locus is very similar between the X chromosome (SEQ ID NO:2) and the Y chromosome (SEQ ID NO:3). The identification of the X or the Y chromosome is based upon an additional six nucleobases present within intron 1 of the Y chromosome but absent in intron 1 of the X chromosome. PCR primers flanking the six basepair addition/deletion region within intron 1 results in the amplicon from the X chromosome Amelogenin allele to be 6 nucleobases shorter than the amplicon from the Y chromosome Amelogenin allele (FIG. 3). This method would not necessarily distinguish differences, if present, in these alleles on the X chromosomes in a female sample because females comprise two X chromosomes and lack a Y chromosome.

Other provided embodiments include, a primer set flanking the six basepair insertion/deletion in the Y/X chromosomes, respectively, of the Amelogenin gene and can include a third primer functioning as a second reverse primer to amplify a variant X chromosome allele(s).

The conservation of the Amelogenin gene across mammalian species is well documented. Frequently, a nucleic acid sample from a human is contaminated with nucleic acid from the human's domestic dog, cat, horse and so on. Thus, in some embodiments, decreasing the length of the reverse primer (SEQ ID NO:8) was found to not only eliminated much of the cross-species reaction but, unexpectedly, revealed the previously unknown single nucleotide polymorphism (SNP) within intron 1 of the Amelogenin gene on the X chromosome. DNA samples from non-primates (10 ng each from mouse, rat, rabbit, sheep, hamster, dog, pig, cat, horse, chicken and bovine) were subjected to PCR amplification as described in Example 1 (using the NGM™ kit) in duplicates for 29 cycles. A cross-reactive peak was only detected in the horse Amelogenin region. Allele peaks were interpreted when the peak was greater than or equal to 50 relative fluorescence units (RFUs) (data not shown). Therefore, contrary to the expectations of a person skilled in the art, in which a longer primer provides greater specificity and sensitivity, a shorter primer was shown to be more sensitive and specific than a longer primer.

In some embodiments, the 3' terminus nucleobase in the reverse primer can be either the variant nucleobase (a thymidine, T or its compliment, an adenine, A) or a universal base. As known to one of skill in the art, a universal base can bind to any nucleobase. Exemplary universal bases for use herein include, but are not limited to, Inosine, Xanthosine, 3-nitropyrrole (Bergstrom et al., Abstr. Pap. Am. Chem. Soc. 206 (2):308 (1993); Nichols et al., Nature 369:492-493; Bergstrom et al., J. Am. Chem. Soc. 117:1201-1209 (1995)), 4-nitroindole (Loakes et al., Nucleic Acids Res., 22:4039-4043 (1994)), 5-nitroindole (Loakes et al. (1994)), 6-nitroindole (Loakes et al. (1994)); nitroimidazole (Bergstrom et al., Nucleic Acids Res. 25:1935-1942 (1997)), 4-nitropyrazole (Bergstrom et al. (1997)), 5-aminoindole (Smith et al., Nucl. Nucl. 17:555-564 (1998)), 4-nitrobenzimidazole (Seela et al., Helv. Chim. Acta 79:488-498 (1996)), 4-aminobenzimidazole (Seela et al., Helv. Chim. Acta 78:833-846 (1995)), phenyl C-ribonucleoside (Millican et al., Nucleic Acids Res. 12:7435-7453 (1984); Matulic-Adamic et al., J. Org. Chem. 61:3909-3911 (1996)), benzimidazole (Loakes et al., Nucl. Nucl. 18:2685-2695 (1999); Papageorgiou et al., Helv. Chim. Acta 70:138-141 (1987)), 5-fluoroindole (Loakes et al. (1999)), indole (Girgis et al., J. Heterocycle Chem. 25:361-366 (1988)); acyclic sugar analogs (Van Aerschot et al., Nucl. Nucl. 14:1053-1056 (1995); Van Aerschot et al., Nucleic Acids Res. 23:4363-4370 (1995); Loakes et al., Nucl. Nucl. 15:1891-1904 (1996)), including derivatives of hypoxanthine, imidazole 4,5-dicarboxamide, 3-nitroimidazole, 5-nitroindazole; aromatic analogs (Guckian et al., J. Am. Chem. Soc. 118:8182-8183 (1996); Guckian et al., J. Am. Chem. Soc. 122:2213-2222 (2000)), including benzene, naphthalene, phenanthrene, pyrene, pyrrole, difluorotoluene; isocarbostyril nucleoside derivatives (Berger et al., Nucleic Acids Res. 28:2911-2914 (2000); Berger et al., Angew. Chem. Int. Ed. Engl., 39:2940-2942 (2000)), including MICS, ICS; hydrogen-bonding analogs, including N8-pyrrolopyridine (Seela et al., Nucleic Acids Res. 28:3224-3232 (2000)); and LNAs such as aryl-.beta.-C-LNA (Babu et al., Nucleosides, Nucleotides & Nucleic Acids 22:1317-1319 (2003); WO 03/020739). The universal base may include those disclosed by Loakes, Nucl. Acids Res., 29: 2437-2447 (2001); and Wu et al, JACS, 22: 7621-7632 (2000), all of which are hereby incorporated by reference herein.

A suitable universal base at the 3' terminus of the PCR primer permits primer binding and extension of the primer from both alleles of the Amelogenin SNP and so generation of the amplicon for which the primers are designed when the allelic variant is either present or when it is absent. As illustrated in FIG. 2, the amplicon in the X chromosome variant sequence, SEQ ID NO:1, would amplify with a complementary variant nucleobase present at the 3' position or if a universal base was substituted for the predominant "G" nucleobase, SEQ ID NO:2. In both instances, because there is only the "G" nucleobase within the corresponding region of intron 1 on the Y chromosome, amplification of the Y chromosome occurs and the amplification product is six nucleobase greater in length.

The hybridization of the primer set to the target nucleic acid sequence of the sample is also contingent upon the primer hybridization (annealing) temperature used in the PCR amplification reaction which impacts primer binding specificity. The terms "annealing" and "hybridizing", including without limitation variations of the root words hybridize and anneal, are used interchangeably and mean the nucleotide base-pairing interaction of one nucleic acid with another nucleic acid that results in the formation of a duplex, triplex, or other higher-ordered structure. The primary interaction is typically nucleotide base specific, e.g., A:T, A:U, and G:C, by Watson-Crick and Hoogsteen-type hydrogen bonding. In certain embodiments, base-stacking and hydrophobic interactions may also contribute to duplex stability. Conditions under which primers anneal to complementary or substantially complementary sequences are well known in the art, e.g., as described in Nucleic Acid Hybridization, A Practical Approach, Hames and Higgins, eds., IRL Press, Washington, D.C. (1985) and Wetmur and Davidson, Mol. Biol. 31:349, 1968. In general, whether such annealing takes place is influenced by, among other things, the length of the complementary portion of the primers and their corresponding primer-binding sites in adapter-modified molecules and/or extension products, the pH, the temperature, the presence of mono- and divalent cations, the proportion of G and C nucleotides in the hybridizing region, the viscosity of the medium, and the presence of denaturants. Such variables influence the time required for hybridization. The presence of certain nucleotide analogs or minor groove binders in the complementary portions of the primers and reporter probes can also influence hybridization conditions. Thus, the preferred annealing conditions will depend upon the particular application. Such conditions, however, can be routinely determined by persons of ordinary skill in the art, without undue experimentation. Typically, annealing conditions are selected to allow the disclosed primers to selectively hybridize with a complementary or substantially complementary sequence in their corresponding adapter-modified molecule and/or extension product, but not hybridize to any significant degree to other sequences in the reaction.

In some embodiments, the primer set used to amplify the intron 1 region of the Amelogenin gene is composed of polynucleotide primers. The primers may comprise adenosine (A), thymidine (T), guanosine (G), and cytidine (C), as well as uracil (U). The primer may comprise at least one nucleoside analog for example, but not limited to, inosine, locked nucleic acids (LNA), non-nucleotide linkers, peptide nucleic acids (PNA), universal bases, and phosphoramidites) and nucleosides containing or conjugated to chemical moieties such as radionuclides (e.g., $^{32}P$ and $^{35}S$), fluorescent molecules, minor groove binders (MGBs), or any other nucleoside conjugates known in the art. The primer may consist of at least one nucleoside analog. The primer may consist essentially of at least one nucleoside analog.

Generally, oligonucleotide primers can be chemically synthesized. Primer design and selection is a routine procedure in PCR optimization. One of ordinary skill in the art can easily design specific primers to amplify a target locus of interest, or obtain primer sets from the references listed herein.

As an example of primer selection, primers can be selected by the use of any of various software programs available and known in the art for developing amplification and/or multiplex systems. Exemplary programs include, Primer Express® software (Applied Biosystems, Foster City, Calif.) and Primer3 software (Rozen S, Skaletsky H (2000), "Primer3 on the WWW for general users and for biologist programmers," Krawetz S, Misener S (eds) Bioinformatics Methods and Protocols: Methods in Molecular Biology. Humana Press, Totowa, N.J., pp 365-386). In the example of the use of software programs, sequence information from the region of the locus of interest can be imported into the software. The software then uses various algorithms to select primers that best meet the user's specifications.

In other embodiments, included are primers for amplification of one or more STR loci simultaneously in a single amplification reaction in addition to the Amelogenin locus. Such systems simultaneously targeting several loci for analysis are called "multiplex" systems. Several such systems containing multiple STR loci and the Amelogenin, non-STR locus, have been described. See, e.g., AMPFLSTR® SGM-PLUS™ PCR AMPLIFICATION KIT USER'S MANUAL, Applied Biosystems, pp. i-x and 1-1 to 1-16 (2001); AMPFLSTR® IDENTIFILER® PCR AMPLIFICATION KIT USER'S MANUAL, Applied Biosystems, pp. i-x and 1-1 to 1-10 (2001); J W Schumm et al., U.S. Pat. No. 7,008,771. See J. M. Butler, Forensic DNA Typing, Biology, Technology, and Genetics of STR Markers, $2^{nd}$ Edition, Elsevier, Burlington, (2005).

The present teachings provide for the selection of an appropriate set of loci, primers, and amplification protocols to generate amplified alleles (amplicons) from multiple co-amplified loci, which amplicons can be designed so as not to overlap in size, and/or can be labeled in such a way as to enable one to differentiate between alleles from different loci which do overlap in size. In addition, these methods can be used in the selection of multiple STR loci which are compatible for use with a single amplification protocol. In various embodiments of the present teachings a co-amplification of the Amelogenin locus with at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least 50, at least 60, at least 70, at least 80, at least 90, and at least 100 or more STR loci is envisioned. At least some of the STR loci can have a maximum amplicon size of less than approximately 100 base pairs, less than approximately 150 base pairs, less than approximately 200 base pairs, less than approximately 250 base pairs, or less than approximately 300 base pairs. Primer design consideration include avoiding significant homology between primers to avoid primer-dimer formation. Further information on loci selection, primer design and multiplex amplification systems and protocols can be found in U.S. patent application Ser. No. 12/261,506, incorporated by reference herein in its entirety.

In some embodiments, illustrative primer sets used to amplify the intron 1 region of the Amelogenin gene for gender determination are illustrated in Table 1.

TABLE 1

| SEQ ID NO: | Sequence, 5' to 3' | Chromosome Allele Detected: |
|---|---|---|
| 5 with 6 | ACCCGAGACATTTCTTATC ATCAGAGCTTAAACTGGGAAG | Y Chromosome, intron 1 of the Amelogenin locus |
| 5 with 6 | ACCCGAGACATTTCTTATC ATCAGAGCTTAAACTGGGAAG | X Chromosome-predominant form, intron 1 of the Amelogenin locus |
| 5 with 7 | ACCCGAGACATTTCTTATC ATCAGAGCTTAAACTGGGAAA | X Chromosome-variant form, intron 1 of the Amelogenin locus |
| 5 with 4 | ACCCGAGACATTTCTTATC ATCAGAGCTTAAACTGGGAAN | X Chromosome-predominant or variant form, intron 1 of the Amelogenin locus |

The primer sequences amplify a region of intron 1 in the Amelogenin gene and depending on the specificity required SEQ ID NOS:5, 6 and either 7 or 4 could be used in the same PCR to detect both predominant and variant X chromosome alleles as identified in the claimed invention.

In some embodiments, amplification methods comprise at least one cycle of amplification, for example, but not limited to, the sequential procedures of: hybridizing primers to primer-specific portions of target sequence or amplification products from any number of cycles of an amplification reaction; synthesizing a strand of nucleotides in a template-dependent manner using a polymerase; and denaturing the newly-formed nucleic acid duplex to separate the strands. The cycle may or may not be repeated.

There are many known methods of amplifying nucleic acid sequences including e.g., PCR. See, e.g., PCR Technology: Principles and Applications for DNA Amplification (ed. H. A. Erlich, Freeman Press, NY, N.Y., 1992); PCR Protocols: A Guide to Methods and Applications (eds. Innis, et al., Academic Press, San Diego, Calif., 1990); Mattila et al., Nucleic Acids Res. 19, 4967 (1991); Eckert et al., PCR Methods and Applications 1, 17 (1991); PCR (eds. McPherson et al., IRL Press, Oxford); and U.S. Pat. Nos. 4,683,202, 4,683,195, 4,800,159 4,965,188 and 5,333,675 each of which is incorporated herein by reference in their entireties for all purposes.

Nucleic acid amplification techniques are traditionally classified according to the temperature requirements of the amplification process. Isothermal amplifications are conducted at a constant temperature, in contrast to amplifications that require cycling between high and low temperatures. Examples of isothermal amplification techniques are: Strand Displacement Amplification (SDA; Walker et al., 1992, Proc. Natl. Acad. Sci. USA 89:392 396; Walker et al., 1992, Nuc. Acids. Res. 20:1691 1696; and EP 0 497 272, all of which are incorporated herein by reference), self-sustained sequence replication (3SR; Guatelli et al., 1990, Proc. Natl. Acad. Sci. USA 87:1874 1878), the Qβ. replicase system (Lizardi et al., 1988, BioTechnology 6:1197 1202), and the techniques disclosed in WO 90/10064 and WO 91/03573.

In some embodiments, amplification methods comprise at least one cycle of amplification, for example, but not limited to temperature cycling. Examples of amplification techniques that require temperature cycling are: polymerase chain reaction (PCR; Saiki et al., 1985, Science 230:1350 1354), ligase chain reaction (LCR; Wu et al., 1989, Genomics 4:560 569; Barringer et al., 1990, Gene 89:117 122; Barany, 1991, Proc. Natl. Acad. Sci. USA 88:189 193), ligase detection reaction (LDR), LDR-PCR, strand displacement amplification (Walker et al., Nucleic Acids Res, 20, 1691 (1992); Walker et al., Proc. Nat'l Acad. Sci. U.S.A., 89, 392 (1992)), transcription-based amplification (Kwoh et al., Proc. Nat'l Acad. Sci. U.S.A., 86, 1173 (1989)) and restriction amplification (U.S. Pat. No. 5,102,784), self-sustained sequence replication (or "3SR") (Guatelli et al., Proc. Nat'l Acad. Sci. U.S.A., 87, 1874 (1990)), nucleic acid transcription-based amplification system (TAS), the Qβ replicase system (Lizardi et al., Biotechnology, 6, 1197 (1988)) and Rolling Circle Amplification (see Lizardi et al., Nat Genet. 19:225 232 (1998)), hybridization signal amplification (HSAM), nucleic acid sequence-based amplification (NASBA) (Lewis, R., Genetic Engineering News, 12(9), 1 (1992)), the repair chain reaction (RCR) (Lewis, R., Genetic Engineering News, 12(9), 1 (1992)), boomerang DNA amplification (BDA) (Lewis, R., Genetic Engineering News, 12(9), 1 (1992), and branched-DNA methods. Any of the amplification techniques and methods disclosed herein can be used to practice the claimed invention as would be understood by one of ordinary skill in the art.

As is understood by one of skill in the art, the Taq polymerase used in PCR often adds an extra (non-templated) nucleotide to the 3'-end of the PCR product as the template strand is copied. This non-template addition is most often adenosine (A) and results in a PCR product that is one base pair longer than the actual target sequence. A final incubation step can optionally be added after the temperature cycling steps in PCR to allow for completion of the addition of the 3' A to those strands that were missed by the Taq polymerase during the thermal cycling steps. Alternatively, the primer sequence may be selected so as to control the amount of non-templated adenylation, e.g., the use of 5' GTTTCTT sequences as taught in Brownstein et al. (BioTechniques, 20, 1004-1010, (1996).

In other embodiments, the determination of gender is based on the amplification of the Amelogenin loci of chromosomes X and Y by the polymerase chain reaction method (PCR) resulting in the generation of PCR amplicon(s) and the detection of the amplicon(s). In other embodiments, the amplification of the Amelogenin loci of chromosomes X and Y is based on the amplification by a method selected from the group consisting of the ligase detection reaction method, LDR-PCR, strand displacement amplification, transcription-based amplification, restriction amplification, self-sustained sequence replication, nucleic acid transcription-based amplification system, the Qβ replicase system, Rolling Circle Amplification, hybridization signal amplification, nucleic acid sequence-based amplification, the repair chain reaction, boomerang DNA amplification, and branched-DNA methods. Detection of the amplicon can be via any number of methods, including but not limited to for example, Northern blot (Thomas, P. S., "Hybridization of Denatured RNA and Small DNA Fragments Transferred to Nitrocellulose," Proc. Nat'l. Acad. Sci. USA, 77:5201-05 (1980), which is hereby incorporated by reference in its entirety), Southern blot (Southern, "Detection of Specific Sequences Among DNA Fragments Separated by Gel Electrophoresis," J. Mol. Biol., 98:503-17 (1975), which is incorporated herein by reference in its entirety), PCR, multiplex PCR (Erlich, et. al., "Recent Advances in the Polymerase Chain Reaction", Science 252: 1643-51 (1991), which is incorporated herein by reference in its entirety), in-situ hybridization (Nucleic Acid Hybridization: A Practical Approach, Haimes and Higgins, Eds., Oxford:IRL Press (1988), which is hereby incorporated by reference in its entirety), in-situ PCR (Haase et al., "Amplification and Detection of Lentiviral DNA Inside Cells," Proc. Natl. Acad. Sci. USA, 87(13):4971-5 (1991), which is hereby incorporated by reference in its entirety), or other suitable hybridization assays known in the art. The amplification of the target nucleic acid and detecting may be carried out using well known sequence-specific amplification methods well-known to persons skilled in the art, and detected by methods including, but not limited to, gel electrophoresis, capillary electrophoresis array-capture, direct sequencing, and mass spectrometry.

Various methods can be used to analyze the products of the amplified alleles in the mixture of amplification products obtained from the multiplex reaction including, for example, detection of fluorescent labeled products, detection of radioisotope labeled products, silver staining of the amplification products, or the use of DNA intercalator dyes such as ethidium bromide (EtBr) and SYBR® Green cyanine dye to visualize double-stranded amplification products. Fluorescent labels suitable for attachment to primers for use in the present teachings are numerous, commercially available, and well-known in the art. With fluorescent analysis, at least one fluorescent labeled primer can be used for the amplification of each locus. Fluorescent detection may be desirable over radioactive methods of labeling and product detection, for example, because fluorescent detection does not require the use of radioactive materials, and thus avoids the regulatory and safety problems that accompany the use of radioactive materials. Fluorescent detection with labeled primers may also be selected over other non-radioactive methods of detection, such as silver staining and DNA intercalators, because fluorescent methods of detection generally reveal fewer amplification artifacts than do silver staining and DNA intercalators. This is due in part to the fact that only the amplified strands of DNA with labels attached thereto are detected in fluorescent detection, whereas both strands of every amplified product are stained and detected using the silver staining and intercalator methods of detection, which result in visualization of many non-specific amplification artifacts.

In some embodiments employed, fluorescent labeling of primers in a multiplex amplification reaction, generally at least two different labels, at least three different labels, at least four different labels, at least five different labels, and at least six or more than seven different labels can be used to label the two, three, four, five or at least six different primers or more primers. When a size marker is used to evaluate the products of the multiplex reaction, the primers used to prepare the size marker may be labeled with a label different from labels of the primers that amplify the loci of interest in the reaction. With the advent of automated fluorescent imaging and analysis, faster detection and analysis of multiplex amplification products can be achieved.

In some embodiments of the present teaching, a fluorophore can be used to label at least one primer of the multiplex amplification, e.g. by being covalently bound to the primer, thus creating a fluorescent labeled primer. In some embodiments, primers for different target loci in a multiplex can be labeled with different fluorophores, each fluorophore producing a different colored product depending on the emission wavelength of the fluorophore. These variously labeled primers can be used in the same multiplex reaction, and their respective amplification products subsequently analyzed together. Either the forward or reverse primer of the pair that amplifies a specific locus can be labeled, although the forward can more often be labeled.

The following are some examples of possible fluorophores well known in the art and suitable for use in the present teachings. The list is intended to be exemplary and is by no means exhaustive. Some possible fluorophores include: fluorescein (FL), which absorbs maximally at 492 nm and emits maximally at 520 nm; N,N,N',N'-tetramethyl-6-carboxyrhodamine (TAMRA™ dye), which absorbs maximally at 555 nm and emits maximally at 580 nm; 5-carboxyfluorescein (5-FAM™ dye), which absorbs maximally at 495 nm and emits maximally at 525 nm; 2',7'-dimethoxy-4',5'-dichloro-6-carboxyfluorescein (JOE™ dye), which absorbs maximally at 525 nm and emits maximally at 555 nm); 6-carboxy-X-rhodamine (ROX™ dye), which absorbs maximally at 585 nm and emits maximally at 605 nm; CY3™ dye, which absorbs maximally at 552 nm and emits maximally at 570 nm; CY5™ dye, which absorbs maximally at 643 nm and emits maximally at 667 nm; tetrachloro-fluorescein (TET™ dye), which absorbs maximally at 521 nm and emits maximally at 536 nm; and hexachloro-fluorescein (HEX™ dye), which absorbs maximally at 535 nm and emits maximally at 556 nm; NED™ dye, which absorbs maximally at 546 nm and emits maximally at 575 nm; 6-FAM™ dye, which emits maximally at approximately 520 nm; VIC® dye which emits maximally at approximately 550 nm; PET® dye which emits maximally at approximately 590 nm; LIZ® dye, which emits maximally at approximately 650 nm, and SID™, TED™ and TAZ™ dyes. See SR Coticone et al., U.S. Pat. No. 6,780,588; AMP-FLSTR® IDENTIFILER® PCR AMPLIFICATION KIT USER's MANUAL, pp. 1-3, Applied Biosystems (2001). Note that the above listed emission and/or absorption wavelengths are only examples and should be used for general guidance purposes only; actual peak wavelengths may vary for different applications and under different conditions.

Various embodiments of the present teachings may comprise a single multiplex system comprising at least four different dyes. These at least four dyes may comprise any four of the above-listed dyes, or any other four dyes capable of producing signals that can be distinguished from one another, e.g., 6-FAM™, VIC®, NED™ and PET® dyes. Other embodiments of the present teaching may comprise a single multiplex system comprising at least five different dyes. These at least five dyes may comprise any five of the above-listed dyes, or any other five dyes capable of producing signals that can be distinguished from one another, e.g., 6-FAM™, VIC®, NED™, PET® and LIZ® dyes. Other embodiments of the present teaching may comprise a single multiplex system comprising at least six different dyes. These at least six dyes may comprise any six of the above-listed dyes, or any other six dyes capable of producing signals that can be distinguished from one another, e.g., 6-FAM™, VIC®, NED™, PET®, LIZ® dyes and a sixth dye (SID™) with maximum emission at approximately 620 nm. The various embodiments of the subject method and compositions are not limited to any fixed number of dyes.

The PCR products can be analyzed on a sieving or non-sieving medium. In some embodiments of these teachings, for example, the PCR products can be analyzed by electrophoresis; e.g., capillary electrophoresis, as described in H. Wenz et al. (1998), GENOME RES. 8:69-80 (see also E. Buel et al. (1998), J. FORENSIC SCI. 43:(1), pp. 164-170)), or slab gel electrophoresis, as described in M. Christensen et al. (1999), SCAND. J. CLIN. LAB. INVEST. 59(3): 167-177, or denaturing polyacrylamide gel electrophoresis (see, e.g., J. Sambrook et al. (1989), in MOLECULAR CLONING: A LABORATORY MANUAL, SECOND EDITION, Cold Spring Harbor Laboratory Press, Cold Spring Harbor, N.Y., pp. 13.45-13.57). The separation of DNA fragments in electrophoresis is based primarily on differential fragment size. Amplification products can also be analyzed by chromatography; e.g., by size exclusion chromatography (SEC).

The size of the alleles present at each locus in the DNA sample can be determined by comparison to a size standard in electrophoresis, such as a DNA marker of known size. Markers for evaluation of a multiplex amplification containing two or more polymorphic STR loci may also comprise a locus-specific allelic ladder or a combination of allelic ladders for each of the loci being evaluated. See, e.g., C. Puers et al. (1993), AM. J. HUM. GENET. 53:953-958; C. Puers et al. (1994), GENOMICS 23:260-264. See also, U.S. Pat. Nos. 5,599,666; 5,674,686; and 5,783,406 for descriptions of some allelic ladders suitable for use in the detection of STR loci, and some methods of ladder construction disclosed therein. Following the construction of allelic ladders for individual loci, the ladders can be electrophoresed at the same time as the amplification products. Each allelic ladder co-migrates with the alleles from the corresponding locus.

The products of the multiplex reactions of the present teachings can also be evaluated using an internal lane standard; i.e., a specialized type of size marker configured to be electrophoresed, for example, in the same capillary as the amplification products. The internal lane standard can comprise a series of fragments of known length. The internal lane standard can also be labeled with a fluorescent dye, which is distinguishable from other dyes in the amplification reaction.

The lane standard can be mixed with amplified sample or size standards/allelic ladders and electrophoresed with either, in order to compare migration in different lanes of gel electrophoresis or different capillaries of capillary electrophoresis. Variation in the migration of the internal lane standard can serve to indicate variation in the performance of the separation medium. Quantitation of this difference and correlation with the allelic ladders can provide for calibration of amplification product electrophoresed in different lanes or capillaries, and correction in the size determination of alleles in unknown samples.

Where fluorescent dyes are used to label amplification products, the electrophoresed and separated products can be analyzed using fluorescence detection equipment such as, for example, the ABI PRISM® 310 or 3130xl genetic analyzer, or an ABI PRISM® 377 DNA Sequencer (Applied Biosystems, Foster City, Calif.); or a Hitachi FMBIO™ II Fluorescent Scanner (Hitachi Software Engineering America, Ltd., South San Francisco, Calif.). In various embodiments of the present teachings, PCR products can be analyzed by a capillary gel electrophoresis protocol in conjunction with such electrophoresis instrumentation as the ABI PRISM® 3130xl genetic analyzer (Applied Biosystems), and allelic analysis of the electrophoresed amplification products can be performed, for example, with GeneMapper® ID Software v3.2, from Applied Biosystems. In other embodiments, the amplification products can be separated by electrophoresis in, for example, about a 4.5%, 29:1 acrylamide:bis acrylamide, 8 M urea gel as prepared for an ABI PRISM® 377 Automated Fluorescence DNA Sequencer.

Another suitable assay method, referred to as a 5'-nuclease assay, is described in U.S. Pat. No. 5,210,015; and Holland et al, 1991, Proc. Natl. Acad. Sci. USA 88:7276-7280; both, incorporated herein by reference. In the 5'-nuclease assay, labeled probes are degraded concomitant with primer extension by the 5' to 3' exonuclease activity of the DNA polymerase, e.g., Taq DNA polymerase. Detection of probe breakdown product indicates both that hybridization between probe and target DNA occurred and that the amplification reaction occurred. The method of real-time PCR utilizes the 5'-nuclease assay method and allows for the simultaneous detection and quantification of DNA in a sample at each PCR cycle. The incorporation of a fluorescently labeled reporter probe into the PCR reaction permits specific and reliable quantification of the target DNA being amplified.

An alternative method for detecting the amplification of nucleic acid by monitoring the increase in the total amount of double-stranded DNA in the reaction mixture is described in Higuchi et al., 1992, BioTechnology 10:413-417; Higuchi et al., 1993, BioTechnology 11:1026-1030; and European Patent Publication Nos. 487,218 and 512,334, each incorporated herein by reference. The detection of double-stranded target DNA relies on the increased fluorescence that ethidium bromide (EtBr) and other DNA binding labels exhibit when bound to double-stranded DNA. The increase of double-stranded DNA resulting from the synthesis of target sequences results in a detectable increase in fluorescence. A problem in this method is that the synthesis of non-target sequence, i.e., non-specific amplification, results in an increase in fluorescence which interferes with the measurement of the increase in fluorescence resulting from the synthesis of target sequences. Thus, the methods as disclosed herein are useful because they reduce non-specific amplification, thereby minimizing the increase in fluorescence resulting from the amplification of non-target sequences. The embodiments described herein provide sensitivity and specificity of detection.

In certain embodiments, detecting comprises an instrument, i.e., using an automated or semi-automated detecting means that can, but need not, comprise a computer algorithm. In certain embodiments, a detecting instrument comprises or is coupled to a device for graphically displaying the intensity of an observed or measured parameter of an extension product or its surrogate on a graph, monitor, electronic screen, magnetic media, scanner print-out, or other two- or three-dimensional display and/or recording the observed or measured parameter. In certain embodiments, the detecting step is combined with or is a continuation of at least one separating step, for example, but not limited to, a capillary electrophoresis instrument comprising at least one fluorescent scanner and at least one graphing, recording, or readout component; a chromatography column coupled with an absorbance monitor or fluorescence scanner and a graph recorder; a chromatography column coupled with a mass spectrometer comprising a recording and/or a detection component; or a microarray with a data recording device such as a scanner or CCD camera. In certain embodiments, the detecting step is combined with an amplifying step, for example, but not limited to, real-time analysis such as Q-PCR.

In certain embodiments, the detecting step is combined with an amplifying step, for example, but not limited to, a melt curve determination. Exemplary means for performing a detecting step include the ABI PRISM® Genetic Analyzer instrument series, the ABI PRISM® DNA Analyzer instrument series, the ABI PRISM® Sequence Detection Systems instrument series, and the Applied Biosystems Real-Time PCR instrument series (all from Applied Biosystems); and microarrays and related software such as the Applied Biosystems microarray and Applied Biosystems 1700 Chemiluminescent Microarray Analyzer and other commercially available microarray and analysis systems available from Affymetrix, Agilent, and Amersham Biosciences, among others (see also Gerry et al., J. Mol. Biol. 292:251-62, 1999; De Bellis et al., Minerva Biotec. 14:247-52, 2002; and Stears et al., Nat. Med. 9:140-45, including supplements, 2003) or bead array platforms (Illumina, San Diego, Calif.). Exemplary software includes GeneMapper™ Software, GeneScan® Analysis Software, Genotyper® Software, and RapidFinder™ Software (all from Applied Biosystems).

Those in the art understand that the detection techniques employed are generally not limiting. Rather, a wide variety of detection means are within the scope of the disclosed methods and kits, provided that they allow the presence or absence of an amplicon to be determined.

The present teachings are also directed to kits that utilize the methods described above. In some embodiments, a basic kit can comprise a container having one or more locus-specific primers. A kit can also optionally comprise instructions for use. A kit can also comprise other optional kit components, such as, for example, one or more of an allelic ladder directed to each of the specified loci, a sufficient quantity of enzyme for amplification, amplification buffer to facilitate the amplification, divalent cation solution to facilitate enzyme activity, dNTPs for strand extension during amplification, loading solution for preparation of the amplified material for electrophoresis, genomic DNA as a template control, a size marker to insure that materials migrate as anticipated in the separation medium, and a protocol and manual to educate the user and limit error in use. The amounts of the various reagents in the kits also can be varied depending upon a number of factors, such as the optimum sensitivity of the process. It is within the scope of these teachings to provide test kits for use in manual applications or test kits for use with automated detectors or analyzers.

The reference works, patents, patent applications, scientific literature and other printed publications, as well as accession numbers to GenBank database sequences that are referred to herein, are all hereby incorporated by reference in their entirety.

While the principles of this invention have been described in connection with specific embodiments, it should be understood clearly that these descriptions are made only by way of example and are not intended to limit the scope of the invention. What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the disclosed embodiments of the art described, thereby enabling others skilled in the art to understand the various embodiments and various modifications that are suited to the particular use contemplated. It is intended that the scope of what is disclosed be defined by the following claims and their equivalence.

EXAMPLES

PCR Assay Set-up:

Methods of the disclosed invention can be practiced as taught in the AmpFISTR® NGM™ PCR Amplification Kit User's Guide, PN 4425511 (Applied Biosystems), incorporated herein by reference. The method involves thawing the Master Mix and Primer set followed by vortexing each for 3 seconds and then briefly centrifuging to remove any liquid from the caps. A PCR reaction mix is prepared based on the following calculation per reaction:

| Component | Volume per reaction |
|---|---|
| PCR Master Mix (2.5X) | 10 μL |
| Primer Set (5X) | 5 μL |

An additional 3 reactions are included in the calculation to provide excess volume for the loss that occurs during reagent transfers. Again, thorough mixing by vortexing at medium speed for 10 sec. followed by briefly centrifuging to remove any liquid from the cap of the vial containing the PCR reaction mix. 15 uL of the PCR reaction mix is aliquoted into each reaction vial or well followed by addition of each sample to be analyzed into its own vial or well, up to 10 uL volume to have approximately 1.0 ng sample DNA/reaction. Samples of less than 10 uL are made up to a final 10 uL volumen with Low-TE Buffer. Following sample addition the tubes or wells are covered and a brief centrifugation at 3000 rpm for about 30 seconds is performed to remove any air bubbles prior to amplification.

The samples are amplified according to specifications found in the User Guide above. When using the GeneAmp PCR System 9700 with either 96-well silver or gold-plated silver block, select the 9600 Emulation Mode. Thermal cycling conditions are an initial incubation step at 95° C. for 11 min., 29 cycles of 94° C. for 20 sec. denaturing and 59° C. for 3 min. annealing followed by a final extension at 60° C. for 10 min. and final hold at 4° C. indefinitely. Following completion, the samples should be protected from light and stored at 2 to 8° C. if the amplified DNA will be analyzed within 2 weeks or at −15 to −20° C. if use is greater than 2 weeks.

The amplified samples are analyzed by methods that resolve amplification product size and/or sequence differences as would be known to one of skill in the art. For example, capillary electrophoresis can be used following the instrument manufactures directions. Briefly, 0.3 uL GeneScan-500 LIZ™ Size Standard and 8.7 uL of Hi-Di Formamide is mixed for each sample to be analyzed. 9.0 uL of the Formamide/GeneScan-500 LIZ solution is dispensed into each well of a MicroAmp® Optical 96-well reaction plate to which a 1.0 uL aliquot of the PCR amplified sample or allelic ladder is added and the plate is covered. The plate is briefly centrifuged to mix the contents and collect them at the bottom of the plate. The plate is heated at 95° C. for 3 minutes and then immediately placed on ice for 3 minutes. Following instrument set-up according to the manufacture's directions each sample is injected and analyzed by appropriate software, e.g., GeneMapper® ID Software v3.2 or GeneMapper® ID-X Software following manufacturers directions.

We claim:

1. A kit comprising a first primer and a second primer, wherein the first primer and the second primer form a PCR primer pair, wherein an amplicon generated by the PCR primer pair includes intron 1 of the amelogenin gene, and wherein the 3' terminal nucleotide of the first primer is complementary to the thymidine at position 83 of SEQ ID NO:1 wherein at least one of the primers is labeled.

2. The kit according to claim 1, wherein the first primer is SEQ ID NO:7.

3. The kit of claim 1, further comprising a third primer, wherein the 3' terminal nucleotide of the third primer is complementary to the cytosine at position 83 of SEQ ID NO:2.

4. The kit of claim 3, wherein the third primer is SEQ ID NO:6.

5. The kit of claim 1, wherein the label is a fluorescent label.

* * * * *